United States Patent [19]

Muthusamy et al.

[11] Patent Number: 5,583,263
[45] Date of Patent: Dec. 10, 1996

[54] PROCESS OF MAKING KETONES

[75] Inventors: Duraisamy Muthusamy, Houston; Chia-Chung Wang, Katy; Richard D. Swain; David B. Litzen, both of Houston; William R. Pledger, Pearland, all of Tex.

[73] Assignee: Shell Oil Company, Houston, Tex.

[21] Appl. No.: 520,950

[22] Filed: Aug. 30, 1995

[51] Int. Cl.$^6$ ..................................................... C07C 45/62
[52] U.S. Cl. ........................... 568/396; 568/390; 568/392
[58] Field of Search .................................... 568/390, 392, 568/396

[56] References Cited

U.S. PATENT DOCUMENTS

| | | | |
|---|---|---|---|
| 2,889,369 | 6/1959 | Dodat | 568/396 |
| 3,045,048 | 7/1962 | Maisel et al. | 568/390 |
| 3,248,428 | 4/1966 | Porter et al. | 568/396 |
| 3,449,435 | 6/1969 | Kudo et al. | 568/396 |
| 3,491,122 | 1/1970 | Schleppnik et al. | 568/392 |
| 3,829,495 | 8/1974 | Mizutani et al. . | |
| 3,946,079 | 3/1976 | Mizutani et al. . | |
| 4,005,147 | 1/1977 | Fischer et al. . | |
| 4,049,571 | 9/1977 | Nissen et al. . | |
| 4,086,188 | 4/1978 | Reichle . | |
| 4,102,930 | 7/1978 | Deem . | |
| 4,146,581 | 3/1979 | Nissen et al. . | |
| 4,165,339 | 8/1979 | Reichle . | |
| 4,170,609 | 10/1979 | Turner . | |
| 4,201,562 | 10/1987 | Olson . | |
| 4,212,825 | 7/1980 | Nissen et al. . | |
| 4,215,076 | 7/1980 | Stueben et al. . | |
| 4,239,657 | 12/1980 | Nissen et al. . | |
| 4,270,006 | 5/1981 | Heilen et al. . | |
| 4,476,324 | 10/1984 | Reichle . | |
| 4,501,918 | 2/1985 | Klemarczyk . | |
| 4,694,108 | 9/1987 | Elliott . | |
| 4,704,480 | 11/1987 | Gefri et al. . | |
| 4,739,122 | 4/1988 | Letts . | |
| 4,866,210 | 9/1989 | Hoelderich et al. . | |
| 4,885,395 | 12/1989 | Hoelderich et al. . | |
| 4,970,191 | 11/1990 | Schutz . | |
| 5,055,620 | 10/1991 | Shutz . | |
| 5,243,081 | 9/1993 | Ishino et al. . | |

FOREIGN PATENT DOCUMENTS

| | | |
|---|---|---|
| 839764 | 4/1970 | Canada . |
| 1191854 | 6/1967 | European Pat. Off. . |
| 1192458 | 8/1967 | European Pat. Off. . |
| 1192570 | 8/1967 | European Pat. Off. . |
| 1252335 | 7/1969 | Japan . |
| 61-5040 | 1/1986 | Japan . |
| 4230342 | 8/1992 | Japan . |

*Primary Examiner*—James H. Reamer
*Attorney, Agent, or Firm*—Todd F. Volyn

[57] ABSTRACT

A multistep process for producing amyl ketones is provided. In the process, a methyl ketone is reacted with butyraldehyde to form a $C_7$ aldol condensation product which is then dehydrated to form an olefinic ketone and hydrogenated to form an amyl ketone. The process is suitable for coproduction along with the production of MIBK and yields products with a high selectivity.

5 Claims, 2 Drawing Sheets

PROCESS OF MAKING KETONES

FIELD OF THE INVENTION

This invention relates to the production of ketones.

BACKGROUND OF THE INVENTION

In aldol condensations, a compound having an alcohol and an aldehyde or ketone group is synthesized from the condensation of two aldehydes, two ketones, or a ketone and an aldehyde. Such reactions are commercially important in the production of intermediates needed to synthesize other commercially important products. Further, many of the aldehydes and ketones that result from application of aldol processes are attractive for use as solvents due to the significant polarity they exhibit.

Unfortunately, aldol condensation reactions have shown a proclivity for nonspecificity. Typically, numerous competing reactions occur creating a large array of cross reacted products. Many of these cross aldol products can be further engineered to ultimately produce either the product that was initially sought or some other desirable product. However, even if useful products can be made from these cross reacted species, their presence complicates batch processes. Moreover, a greater amount of feed stock is necessary to obtain final product from a process which produces cross reacted products.

Each cross reacted species represents added cost to the production of solvents because more varied and numerous equipment is required. This includes additional distillation columns and reactors, additional reagents, and additional catalysts. This is particularly true in one step aldol processes. The numerous products that result from these reactions are frequently of similar molecular weight, polarity, and boiling point. This makes separation extremely difficult and makes commercialization of these processes particularly troublesome and expensive.

Methyl Isobutyl Ketone (4-methyl-2-pentanone, hereafter MIBK), has been a particularly important solvent produced by a combination of aldol condensation, dehydration, and selective hydrogenation reactions. MIBK has been extensively used as a solvent in coatings, paints, rare metal extractions, as a denaturant, and in other applications.

Environmental concerns have recently prompted the search for effective alternatives to MIBK. Methyl n-amyl ketone (MNAK) and several other ketones have been found to have many of the same desirable characteristics as MIBK with a lessened environmental impact. This has caused a surge in the demand for such ketones that is likely to continue to grow. Supplying this demand for MIBK replacements presents a significant challenge.

The development of safe and efficient processes for the commercial production of MIBK has been one of the resounding success stories of the chemical industry. MIBK production process can be conducted in three steps. First, acetone (dimethyl ketone, hereafter "DMK") is treated with an alkali catalyst to produce diacetone alcohol (hereafter "DAA"). This DAA is then acid-catalyzed to dehydrate into mesityl oxide (hereafter "MO") which is selectively hydrogenated over a Nickel or Copper containing catalyst to produce MIBK.

Many of the facilities producing MIBK currently in use have been operating for several decades. Of course, efforts aimed at improving the economics of MIBK production and ketone production in general have been continuous. A great deal of effort in this regard has been applied to the development of one-step reactions. In the typical one-step process for the production of MIBK, a mixture of acetone and hydrogen are reacted in the presence of a catalyst system comprised of a zeolite impregnated with a metal such as palladium or nickel to produce the end product ketone. Other catalysts and catalyst systems have been proposed but most involve fairly specialized chemistries. Further, difficulties are encountered in separating and refining products of these one-step reactions as noted above. The limitation of cross reactivity to a manageable number of separable products is due to the specificity of the catalyst used in these reactions.

Examples of one-step aldol processes include British Patent 1,252,335 to Sumitomo Chemical Co. This patent is drawn to a one-step vapor phase aldol condensation of acetone to obtain MIBK. U.S. Pat. No. 4,866,210 to Hoelderich, et. al. is drawn to a one-step reaction for producing unsymmetrical (aliphatic ketones by an aldol reaction catalyzed by an acid catalyst supported by a zeolite or aluminum phosphate carrier. U.S. Pat. No. 4,102,930 to Deem is drawn to a one-step aldol reaction for producing ketones and aldehydes in which a particular catalyst is claimed. U.S. Pat. No. 4,701,562 to Olson is drawn to a one-step process for condensing aldehydes catalyzed by a nonzeolitic aluminophosphate. U.S. Pat. No. 5,055,620 to Letts is drawn to a one-step aldol condensation reaction in which a pseudoboehmite borne catalyst is employed.

U.S. Pat. No. 4,739,122 ('122) to Letts proposes a cross-aldol condensation for producing Methyl Amyl Ketone (MAK) using a hydrogen reduced copper oxide on gamma alumina catalyst. The product of the process is a mixture of closely related ketones many of which appear in extremely small quantities. "Useful products" in this patent are defined as a mixture of at least four different ketones (MAK, Ethyl Hexaldehyde, Diamyl Ketone, and MIBK). At least three components in this mixture are byproducts that are produced in small quantity (Ethyl Hexaldehyde, Diamyl Ketone, and MIBK). U.S. Pat. No. 4,239,657 ('657) to Nissen, et. al. proposes a one-step process for making aldehydes and ketones of not less than four carbons. A cobalt/nickel/zinc oxide/metallic catalyst on a support is claimed with great particularity. The processes disclosed in the '122 and '657 patents produce, in addition to MIBK, certain products which are referred to throughout this specification as ketone and aldehyde byproducts. These ketone and aldehyde byproducts include 4-methyl-3-penten-2-one; 3-heptene-2-one; undecan-6-one; 4-undecen-6-one; 4,7-undecadien-6-one; and butyl butyrate. In the processes proposed, these chemical species are largely unusable yield losses.

A number of patents are directed solely to catalysts used to improve the selectivities and yields of aldol condensations. U.S. Pat. No. 4,165,339 to Reichle describes a complex catalyst system for improving the performance of known aldol condensation processes particularly those that produce mesityl oxide and isophorone from acetone; U.S Pat. No. 4,146,581 to Nissen, et. al. describes a catalyst system for producing higher ketones; U.S. Pat. No. 4,270,006 to Heilen, et al. describes a catalyst system largely incorporating noble metals and salts of rare earth metals; U.S. Pat. No. 4,049,571 to Nissen, et. al. describes another catalyst for one-step aldol condensations that yield higher ketones; U.S. Pat. No. 4,086,188 to Reichle describes such a catalyst comprised of an alkaline metal or alkaline earth metal and a doped solution of water with a zinc or lithium salt while his U.S. Pat. No. 4,476,324 is directed to a heat treated anionic clay mineral for the same purpose.

Selective catalysts can generally be used to produce either MIBK or MNAK. Producing both concurrently in the same reaction vessels or production setups according to one-step processes has not been commercially successful. Further, since aldol condensations generally produce a complex mixture of cross reacted products, separating such aldol products would be expected to involve process engineering that is specific to the desired product. Even if one could successfully produce both MIBK and MNAK simultaneously, the process redesign and additional new separation technologies required would be substantial and difficult.

While the demand for MNAK may surpass that of MIBK, it will probably not supplant it entirely. Numerous applications for which MIBK is particularly well suited will continue for years to come. Dedicating time, effort, and resources to building MNAK production facilities from existing MIBK facilities or simply establishing separate processes may create a Hobson's choice for those who wish to produce both MNAK and MIBK. They must either invest substantial capital in the production of new and separate production facilities or they must reequip their MIBK facilities to such a degree that MIBK can no longer be produced in commercially meaningful quantities. This could quickly make the production of MIBK replacement ketones an economically unattractive proposition for a manufacturer.

A method of producing high value ketones such as MNAK from existing MIBK production facilities would provide an economic means for producing both MIBK and MNAK. Such a process employing easily obtainable catalysts without the need for extensive separation steps would be more desirable yet. Moreover, coproduction of such high value ketones would greatly reduce duplication of effort and provide manufacturers flexibility in ketone production.

SUMMARY OF THE INVENTION

A process for coproducing $C_7$ ketones by aldol condensation is presented in which one reacts dimethyl ketone and n-butyraldehyde in the presence of a cross aldol catalyst to produce a mixture of diacetone alcohol and 4-hydroxy-2-heptanone which is substantially free of other cross aldol products. The mixture is then dehydrated in the presence of a catalytic quantity of $H_2SO_4$, $NaHSO_4$, or sulfonic acid resins to produce a mixture of mesityl oxide and 3-hepten-2-one. This mixture is then hydrogenated in the presence of a stream of hydrogen and a hydrogenation catalyst to produce a product mixture comprised of methyl iso-butyl ketone and methyl n-amyl ketone. The product mixture is substantially free from aldehyde and ketone byproduct and comprises both MIBK and MNAK.

DETAILED DESCRIPTION OF THE INVENTION

A new method has been found for producing MNAK with a combination of product selectivity and yield heretofore unrecognized in the art. Further, this new method for producing MNAK may largely make use of existing MIBK production means or may be practiced in coproduction with MIBK. This new process does not require the relatively short lived esoteric catalysts found in one step aldol reactions.

As used throughout this specification, coproduction is the simultaneous production of two different desired products from essentially the same physical setup. It will be readily appreciated by those skilled in the art that separate finishing steps and minor adjustments may be made at different points throughout a process to attain the different products desired and still such a process is within the scope and meaning of the term "coproduction."

In the most preferred embodiment of this invention, the existing ketone production processes can be run concurrently with the production of newly produced ketones such as MNAK in a coproduction mode. Existing production processes can also be altered to efficiently and economically produce ketones such as MNAK and MIAK that have not been produced in the existing processes.

The reactants used in the preferred embodiment are DMK and NBAD. They undergo an aldol condensation reaction to produce 4-hydroxy-2-heptanone (4H2H). Without being bound to theory this phase of the process is believed to have three reactions in competition:

One skilled in the art would expect a broad range of products from these reactions. Indeed, this is the case in one-step processes.

In the case of the preferred embodiment of this invention, the self condensation of NBAD is considered the most detrimental to the ultimate selectivity of the process. Thus, it is important to minimize the occurrence of this reaction with respect to the other two. One method that has been used to achieve this result is through the adjustment of reactant concentrations as set forth in more detail below.

A further concern in the aldol reaction is that the products shown in the equations above will undergo further reactions with DAA, DMK feed, NBAD feed, or a combination of these chemical species and other trace products. Again, without being bound to theory, side reactions of this type ordinarily occur in aldol condensation reactions and could be expected to appear here. Commercially producing $C_7$ ketone cross-aldol products that can easily be converted to MNAK and other desired products requires a minimization of the side reactions as well. This will result in producing a product stream which is substantially free of ketone and aldehyde byproduct thereby lessening the expense of complex separations. One skilled in the art will understand that a product stream substantially free of byproduct may nevertheless contain trace amounts of such byproducts.

Figure 1:
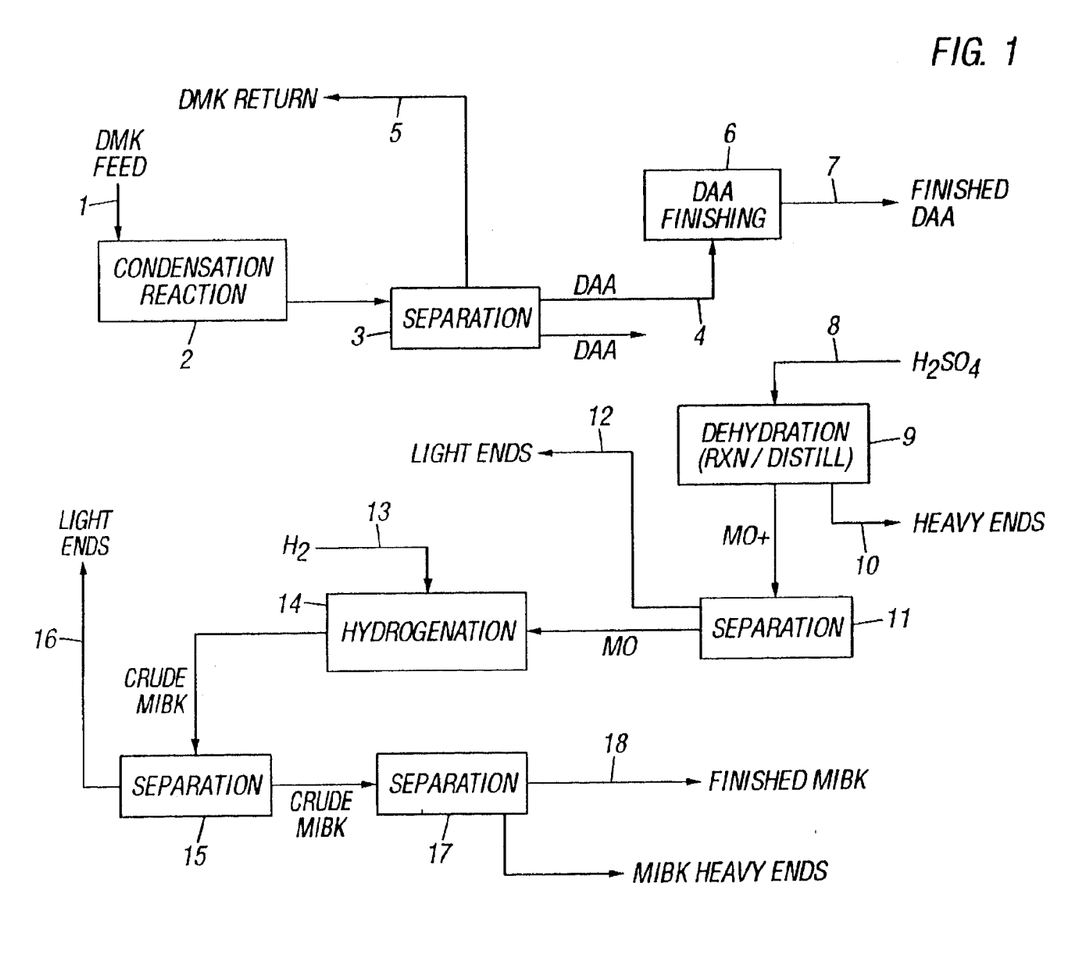
FIG. 1. is a flow diagram showing a multistep process for the production of MIBK.

Turning to the drawings, FIG. 1 is a flow diagram showing an existing process used to produce MIBK. Here, DMK is fed into a Reactor 1 and catalyzed to undergo a condensation reaction 2 to form diacetone alcohol (DAA). DAA and unreacted DMK are then sent through a Separation 3. Any well known method of separation such as distillation can be used here. Unless otherwise noted, this is true of all separation steps throughout this specification. Unreacted DMK is then returned to feed 5. Since DAA is itself a product that is useful both for further processes and as an end product, some of the DAA is withdrawn from the MIBK process. This is then sent to a DAA finishing process 6 with finished DAA being withdrawn at 7.

DAA that is to be further used in the synthesis of MIBK is sent to undergo dehydration in the Reaction/Distillation column 9. $H_2SO_4$ is added at dehydration step 8 to form mesityl oxide (MO). In the column 9, various unwanted byproducts are also generated. These are withdrawn as Heavy Ends 10, which may be used in various other processes or discarded. MO is sent through a further Separation step 11. Light ends 12, comprising DMK which was not removed in the column 9, are extracted from the MO as part of the separation step 11. Purified MO leaving the separation step 11 is then sent to be hydrogenated to a hydrogenation step 14. $H_2$ 13, is injected into the hydrogenation step. Crude MIBK is then formed and sent from the hydrogenation step 14 to another separation step 15. Light Ends 16 are withdrawn in separation step 15 and are used elsewhere for the other processes and products. The MIBK which is withdrawn from Separation step 15 as crude MIBK is then subjected to further separation step 17 from which the finished product, finished MIBK 18 is extracted.

Figure 2:
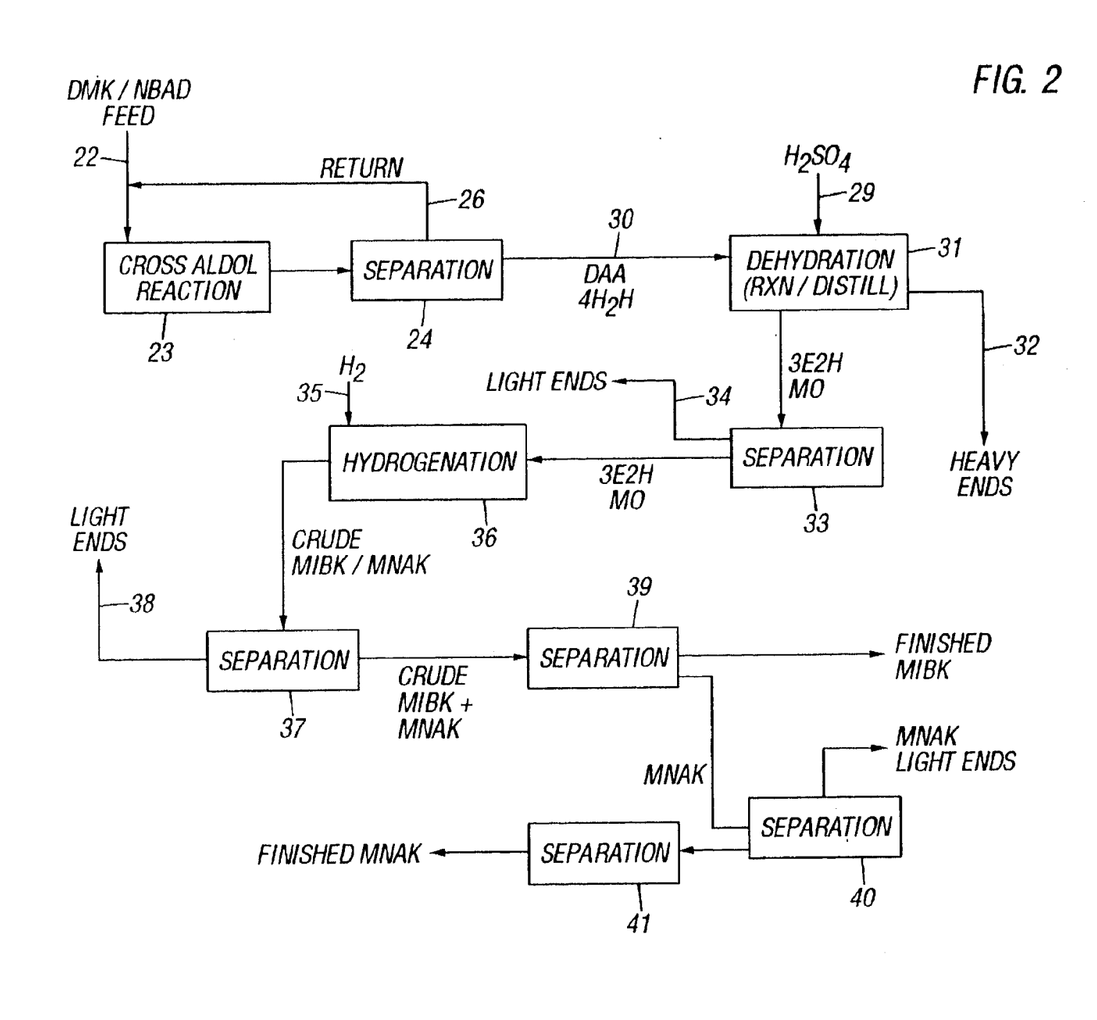
FIG. 2. is a flow diagram for an embodiment of the instant invention in which MNAK and MIBK are coproduced.

FIG. 2 is a flow diagram showing the coproduction of MNAK with MIBK utilizing an existing MIBK production process. NBAD (n-butyraldehyde) and DMK are introduced as a Feed 22 to conduct the Cross Aldol Reaction, 23. It has been found that a feed containing from 0.1 to 25 w % NBAD (by total weight of reactants) is needed to minimize the NBAD self condensation. Preferably, the feed will contain between 1 and 3 w % (by total weight of reactants) NBAD. NBAD feeds are essentially acid free.

Reaction temperatures are set between about 0° and 60° C. Preferably, they are between 10° and 45° C. The pressure under which this step occurs is generally maintained from about 1 to about 10 atmospheres. A large number of basic catalysts may be used to drive this step since it involves a nucleophilic addition. Alkali metal hydroxides, alkaline earth metal hydroxides, alkali metal alkoxides, and alkali earth metal alkoxides work well individually or in combination. Suitable catalysts of these classes of compositions include LiOH, NaOH, LiOEt, NaOEt, $Mg(OH)_2$, $Ca(OH)_2$, $Mg(OEt)_2$, $Ca(OEt)_2$.

Other basic catalysts can also be readily incorporated into this reaction. These catalysts can be used in a solution or can be used as part of a solid state system. Of course, if such catalysts are used in solution appropriate solvents must used. Soda lime is an example of a solid state catalyst system that may be employed in the instant invention.

In a preferred embodiment of this invention, strongly basic ion exchange resin catalysts which could not be used in one-step processes are used in the cross aldol reaction step 23. "AMBERLITE IRA-400," "A-26," and "A-29" (trade names of Rohm and Haas, Inc.), are useful catalysts for this purpose. They are strongly basic catalysts comprised of quaternary ammonium hydroxide catalyst supported on a polymer backbone. A-26 is used in the most preferred embodiment of the present invention. As used throughout this specification, the catalysts which can catalyze the cross-aldol reaction as described above are referred to as cross aldol catalysts.

It is also possible to employ an acid catalyst in the cross-aldol reaction between DMK and NBAD. Conducting the reaction in this manner combines the cross-aldol step together with a dehydration step to produce olefinic ketone, intermediates. Less control over the selectivity of the cross-aldol products results from this process than when a basic catalyst is used, but MNAK product will still be attained. Conducting the process in this manner obviates the need to keep feed NBAD in an acid free state. Fixed bed sulfonic acid resin catalysts have been useful for this purpose.

DAA and 4-hydroxy-2-heptanone (4H2H) are formed in reaction 23. These are separated from unreacted species in Separation step 24. Unreacted DMK and NBAD are returned to feed 26.

A DAA and 4H2H stream 30 is sent to a Dehydration/reaction column 31. $H_2SO_4$ is also sent to column 31 in catalytic quantities. DAA and 4H2H are then dehydrated to form MO and 3E2H (3-heptene-2-one). $NaHSO_4$, sulfonic acid resins such as "M-31" (the trade name for a sulfonic acid resin produced by Dow Chemical Co.), and "AMBERLYST XN-1010" (a trade name for a sulfonic acid resin produced by Rohm and Haas), Inc are examples of other dehydrating agents that may be used in this step.

The reaction temperature in dehydration step 31 is maintained between about 100° to 180° C. with pressures between about 1 and 2 atmospheres. In a most preferred embodiment of this invention, dehydration occurs in a reaction/distillation column.

Heavy ends which are also formed in the dehydration step 31 are withdrawn in heavy ends withdrawal step 32. Care must be exercised here because improper physical conditions in the dehydration process can result in the elimination of a portion of the 3E2H as heavy ends. This can occur where 3E2H is allowed to further react. This problem is avoided by reducing residence time, by raising reaction temperature, or injecting steam. The introduction of steam is the preferred method for avoiding the unnecessary elimination of 3E2H.

MO and 3E2H withdrawn from column 31 are then sent to another separation step 33. Light Ends 34 are then withdrawn and recycled in the process. The separated MO and 3E2H are sent from separation step 33 to undergo a hydrogenation reaction 36 which has a stream of $H_2$ 35, injected therein in the presence of a hydrogenation catalyst. $H_2$ 35 is injected in sufficient quantities to maintain reaction conditions in hydrogenation reaction 36 at between about 300° and 435° F. and between about 25 and 125 psig. The appropriate mixture of temperatures and pressures are selected to retain the intermediates in the vapor phase.

Preferred hydrogenation catalysts include transition metal catalyst systems having active components comprised of Ni, Co, Cu, and Cr; noble metal systems having active components comprised of Pt, Pd, Rh, Ru, Re, and Ir; and combinations of these catalysts. Ni on alumina, Raney-Ni, Pd on carbon, Pd-on-alumina and Pt on silica are especially preferred while a Pd-on-alumina catalyst is the most preferred system.

This hydrogenation reaction 36 yields crude MNAK and MIBK; crude forms of the two principal products sought in the process. They are then separated from light ends 38, in another separation step 37. Crude MNAK and MIBK are then separated in further separation steps 39 to 41 to yield finished MNAK and finished MIBK.

Methyl isoamyl ketone (MIAK) can also be produced according to a coproduction process substantially as described herein. This is done by employing feed comprising i-butyraldehyde (IBAD) rather than NBAD. Aldol cross reaction products are 4-hydroxy-5-methyl-2-hexanone and DAA. Dehydration of DAA and 4-hydroxy-5-methyl-2-hexanone results in the production of MO and 5-methyl-3-hexene-2-one. Selective hydrogenation of MO and 5-methyl-3-hexene-2-one yields MIAK and MIBK.

This invention is further illustrated by the following nonlimiting examples.

EXAMPLES

Unless otherwise noted, the following applies throughout these Examples. A-26 catalyst (Rohm & Haas macroreticular strong base ion exchange resin), and n-butyraldehyde (99%+pure) were purchased from Aldrich Chemical Co. NBAD was freshly distilled under an inert atmosphere just before use. Acetone (DMK), isopropanol (IPA), and methanol (B&J Brand high purity solvents) were purchased from Baxter and used without further purification.

DMK was sparged with Ar to remove air from the solution and the vapor phase of the container just before making the DMK/NBAD mixed feed. Mesityl oxide (99% pure), where needed for analytical purposes, was purchased from Janssen Chimica and used without further purification. Methyl n-amyl ketone (98% pure) and methyl n-amyl carbinol (96% pure) used for comparative analysis was purchased from Aldrich. NaOH solution made in $CO_2$-free deionized water was purchased from Ricca Chemical Co.

The active form of the A-26 catalyst (a quaternary ammonium hydroxide) was either stored in wet form in a tightly closed reactor tube or handled under a flow of Ar during transfers.

Organic compounds were analyzed by Gas Chromatography (GC) methods using DB-5, DX-4, or DB-1701 60 meter capillary columns. GC response factors for the various peaks were obtained by analyzing standards made from pure compounds. GC analysis results were obtained in % weights unless mentioned otherwise. Water concentrations were measured by a Karl-Fischer titration. Acidity measurements on NBAD containing samples were performed under inert atmosphere using IPA as solvent and a 0.04N solution of tetrabutylammonium hydroxide in IPA as titrant.

3-Hepten-2-one (3E2H), 4-hepten-2-one (4E2H), and 5-hepten-2-one (5E2H), the isomers of the $C_7$ unsaturated ketone, are sometimes collectively referred to as 3-hepten-2-one or 3E2H.

EXAMPLE 1

DMK/NBAD Cross-Aldol Reaction over Fixed Bed A-26 Catalyst

A jacketed glass column reactor (consisting of a 0.62" ID×12" catalyst section and 0.25" ID×6" feed preheat section) was loaded with a SiC support/filler bed followed by 16.0 grams of fresh A-26 catalyst in moist form. The catalyst was activated at room temperature by pumping 1.0N NaOH solution through the bed, in upflow mode, at a rate of 0.8 ml/min for a period of 3.0 hours. The catalyst was then washed by pumping $CO_2$-free deionized water at a rate of 1.5–4.0 ml/min until the eluent was neutral to pH test paper.

A DMK/NBAD/$H_2O$ mixed feed was prepared under an inert atmosphere by adding, to a DMK solution that had been sparged with Ar, NBAD that had been freshly distilled under Ar atmosphere and $CO_2$-free deionized water.

A feed of 3460 bed weights (based on 16 g of resin) comprised of 98 w % DMK, 1 w % NBAD, and 1 w % Water (basis total weight of feed) was pumped upflow through the catalyst bed at a WHSV of 5–10. The reaction temperature was maintained in the 10° C. range by circulating through the column jacket a coolant from a temperature controlled water bath. $CO_2$-free deionized water was pumped through the bed in order to fluidize and redistribute the catalyst on two occasions. GC, Karl-Fischer titration, and acid-base titration methods were employed to determine the compositions of feed and product samples. The reaction selectivity and catalyst activity data are shown in Table 1.

This example shows that good reaction selectivity is attainable in a cross aldol reaction between DMK and NBAD. Samples showing a low conversion rate of reactants to products were taken at least 2.5 hours into the run time. Rapid removal of products from the reactor avoids such low conversions. Ultimately, nearly 100% of the DMK is converted as it is recycled into a feed stream to further the conversion of DMK to DAA.

Catalyst life was viable throughout the entire 25 day course of performing this example.

TABLE 1

| | | | | | | | | |
|---|---|---|---|---|---|---|---|---|
| DMK/NBAD Cross-Aldol Reaction over Fixed Bed A-26 Catalyst | | | | | | | | |
| Run Time | WHSV* | Feed H2O | % M Conversions | | Sel, % M NBAD to | | Sel, % M DMK to | |
| (Bed Wt) | (G/G/Hr) | (% W) | DMK | NBAD | C7 | C8 | C6 | C7 |
| 5 | 4.5 | 1 | 11.8 | 100 | 76.9 | 3.1 | 93.2 | 5.2 |
| 10 | 4.6 | 1 | 16.9 | 100 | 57.4 | 1.3 | 95.7 | 2.7 |
| 14 | 4.3 | 1 | 16.4 | 100 | 45.9 | 1.3 | 95.1 | 2.3 |
| 312 | 4.3 | 1 | 16.2 | 100 | 51.4 | 1.5 | 92.6 | 2.8 |
| 320 | 8.5 | 1 | 14.9 | 100 | 62.0 | 1.7 | 94.0 | 3.6 |
| 367 | 4.4 | 1 | 15.9 | 100 | 57.4 | 1.7 | 93.9 | 3.2 |
| 1416 | 5.1 | NA | 9.3 | 97 | 87.8 | 3.0 | 92.0 | 7.7 |
| 1657 | 4.9 | 1 | 16.3 | 100 | 63.6 | 1.5 | 93.0 | 3.0 |
| 1980 | 5.0 | 8 | 14.2 | 100 | 88.2 | 2.8 | 91.5 | 5.0 |
| 3459 | 9.8 | 1 | 6.4 | 86 | 79.1 | 2.0 | 93.8 | 8.2 |

*Based on the moist resin added to reactor

EXAMPLE 2

DMK/NBAD Cross-Aldol Reaction Catalyzed by Aqueous NaOH Solution

A three-necked one-liter round bottom flask with baffles was equipped with an ⅛" line from Altex feed pump for feeding NBAD, reflux condenser, magnetic stirrer, thermometer, and positive $N_2$ atmosphere. The flask was immersed in a constant temperature (24° or 44° C.) water bath. 464.0 grams of DMK was added to the flask and equilibrated with the bath temperature. NaOH (100 ml of 1.0N solution) was added and the NBAD addition was started at a rate of 1.5 ml/minute. 145.4 to 145.9 grams of NBAD was added over a period of 2.0 hours and the reaction was continued for another 30 minutes.

Samples of the reaction mixture were obtained every 30 minutes, shaken with M-31 sulfonic acid resin to remove the NaOH, and analyzed by GC. Results (Table 2) are shown as averages over 120 minutes of reaction.

This example shows that good reaction selectivity is attainable in a cross aldol reaction between DMK and NBAD. Conversion from reactants to products can be made rather completely. DMK is recycled into a feed stream to further the conversion of DMK to DAA.

TABLE 2

| | DMK/NBAD Cross-Aldol Reaction Catalyzed by Aqueous NaOH Solution | | | | | | | |
|---|---|---|---|---|---|---|---|---|
| Run Time | Feed M/M | Rxn Temp | % M Conversions | | Sel, % M NBAD to | | Sel, % M DMK to | |
| (Min) | NBAD/D | (°C.) | DMK | NBAD | C7 | C8 | C6 | C7 |
| 0 | 0.00 | 24 | 0 | 0 | | | | |
| 30 | 0.06 | " | 10 | 92 | 81 | 16 | 50 | 48 |
| 60 | 0.13 | " | 17 | 94 | 76 | 16 | 40 | 54 |
| 90 | 0.19 | " | 21 | 93 | 70 | 19 | 32 | 59 |
| 120 | 0.25 | " | 25 | 92 | 67 | 21 | 26 | 63 |
| 135 | 0.25 | " | 26 | 94 | 67 | 19 | 25 | 62 |
| 0 | 0.00 | 44 | 0 | 0 | | | | |
| 30 | 0.06 | " | 10 | 93 | 85 | 13 | 51 | 48 |
| 70 | 0.15 | " | 16 | 94 | 80 | 14 | 28 | 68 |
| 90 | 0.19 | " | 19 | 94 | 75 | 14 | 22 | 69 |
| 120 | 0.25 | " | 24 | 94 | 70 | 16 | 16 | 70 |

EXAMPLE 3

DMK/NBAD Cross-Aldol Condensation Reaction over Fixed Bed M-31 Sulfonic Acid Resin Catalyst A reactor consisting of a feed pre-heater (jacketed stainless steel tube, ⅛" ID×15"), a reactor tube (jacketed stainless steel tube, 0.5" ID×12", for containing the catalyst) equipped with a thermocouple, a product cooler (jacketed stainless steel tube, ⅛" ID×15"), and a back-pressure regulator was set up.

33.7 grams (46.5 ml in volume) of M-31 sulfonic acid resin catalyst was added to the reactor and the void space above the catalyst was filled with a loose plug of glass wool. The reactor pressure was controlled in the 140–145 PSIG range. The reaction temperature was maintained at a temperature of 75° or 90° C. by circulating, through the jackets around the pre-heater and the reactor, hot water from a temperature controlled water bath. Water was circulated through the jacket around the product cooler.

DMK/NBAD mixed feed containing 1–5% NBAD was pumped through the catalyst bed in upflow mode at a rate of 1.0 to 1.5 ml/minute. Several product fractions were collected under each condition. Samples were analyzed by GC and the results are given in Table 3.

This example shows that the cross aldol reaction can be acid catalyzed.

TABLE 3

| | DMK/NBAD Cross-Aldol Condensation Reaction over Fixed Bed M-31 Sulfonic Acid Resin Catalyst | | | | | | | |
|---|---|---|---|---|---|---|---|---|
| Rxn Temp | NBAD in Feed | Feed Rate | % M Conversions | | Sel, % M NBAD to | | Sel, % M DMK to | |
| (°C.) | (% W) | (WHSV) | DMK | NBAD | C7 | C8 | C6 | C7 |
| 75 | 1 | 2.1 | 10.1 | 46.9 | 55.0 | 4.0 | 95.7 | 2.0 |
| 75 | 1 | 1.4 | 11.6 | 53.2 | 54.0 | 3.9 | 94.7 | 1.9 |
| 90 | 1 | 1.4 | 15.7 | 71.5 | 52.2 | 2.5 | 90.7 | 1.8 |
| 75 | 2 | 1.4 | 11.5 | 54.4 | 53.4 | 8.1 | 94.3 | 4.5 |
| 90 | 2 | 1.4 | 15.3 | 70.7 | 52.3 | 5.5 | 90.6 | 4.3 |
| 75 | 5 | 1.4 | 10.8 | 53.2 | 47.7 | 21.0 | 89.3 | 11.6 |
| 90 | 5 | 1.4 | 14.5 | 65.7 | 50.8 | 15.8 | 85.7 | 11.4 |

EXAMPLE 4

Dehydration of 4-Hydroxy-2-heptanone Using Refluxing Aqueous $H_2SO_4$ as Catalyst To a three-necked 100 ml round bottom flask equipped with a magnetic stirrer, heating mantle, thermometer, overhead condenser and a receiving flask for collecting the product, positive $N_2$ atmosphere, and an ⅛" feed line from Altex pump for feeding 4-hydroxy-2-heptanone (4H2H), was added 51.7 grams of 0.5N $H_2SO_4$ solution.

The solution was heated to 100° C. and then the feed was started at a rate of 1.5 ml/minute. A mixture of the organic product and water started to collect in the receiving flask. The feed (21.85 grams) was added over a period of 16 minutes. The reaction was continued for another 1.25 hours during which time an additional amount of product collected. During the course of the reaction the reaction temperature changed from 99° to 105° C. and the product vapor temperature changed from 97° to 100° C.

After separating the product phases, the organic phase weighed 18.6 grams and the aqueous phase weighed 45.4 grams. After cooling the reaction mixture the organic residue was extracted with ether and the ether solution was evaporated to obtain 0.18 gram of the residue. The feed and product samples were analyzed by GC to determine their area % composition. The 4-hydroxy-2-heptanone to 3-hepten-2-one conversion was 95% with a nearly quantitative (at least 99%) selectivity to product.

This example shows that the reaction products of the cross aldol reaction can be selectively dehydrated to attain good yields of MO and 3E2H. It further shows that the process described in Example 11 can be adjusted to avoid losing 3E2H to heavy ends disposal.

EXAMPLE 5

Dehydration of 4-Hydroxy-2-heptanone Using Refluxing Aqueous $H_2SO_4$ as Catalyst To a three-necked 500 ml round bottom flask equipped with an overhead mechanical stirrer, heating mantle, thermometer, overhead condenser and a receiving flask for collecting the product, positive Ar atmosphere, and an ⅛" feed line from Altex pump for feeding 4-hydroxy-2-heptanone, was added 100 ml of 0.5N $H_2SO_4$ solution.

The solution was heated to 100° C. and then the feed was started at a rate of 1.5 ml/minute. A mixture of the organic product and water started to collect in the receiving flask. The feed (197.4 grams) was added over a period of 2.7 hours. The reaction was continued for another 7.8 hours and during this time the product aqueous phase was periodically pumped back to the reaction mixture. During the course of the reaction the reaction temperature was in the 97°–110° C. range and the product vapor temperature was in the 92°–100° C. range.

The organic phase product weighed 171.1 grams. After cooling the reaction mixture the organic residue was extracted with ether and the ether solution was evaporated to obtain 4.3 grams of the residue. Here too, an excellent yield was obtained. The feed and product samples were analyzed by GC to determine their area% composition. The 4-hydroxy-2-heptanone to 3-hepten-2-one conversion was 99% with a nearly quantitative (at least 99%) selectivity to product.

This example shows that the reaction products of the cross aldol reaction can be selectively dehydrated to attain good yields of MO and 3E2H and the conversion can be very high. It further shows that the process described in Example 11 can be adjusted to avoid losing 3E2H to heavy ends disposal.

EXAMPLE 6

Dehydration of 4-Hydroxy-2-heptanone/Diacetone Alcohol Mixture over M-31 Sulfonic Acid Resin Catalyst A 1.0:1.0 molar mixture of 4-hydroxy-2-heptanone and diacetone alcohol (1.1 grams) and a small magnet were added to a septum capped vial. The vial was placed on a magnetic stirrer which was immersed in a temperature controlled water bath. After heating the solution to the reaction temperature (50° or 65° C.), 0.1 gram of M-31 sulfonic acid resin catalyst was added. Liquid samples (0.5 microliter) of the reaction were taken with the use of a GC syringe and analyzed by GC. Reaction time was 4.5 hours. The results are given in Table 4.

This example shows that the reaction products of the cross aldol reaction can be selectively dehydrated to attain good yields of MO and 3E2H. It further shows that the process described in Example 11 can be adjusted to avoid losing 3E2H to heavy ends disposal. DAA and 4H2H have the same reaction rate.

TABLE 4

Dehydration of 4-Hydroxy-2-heptanone/Diacetone Alcohol Mixture over M-31 Sulfonic Acid Resin Catalyst

| Rxn Time (Min) | Temp (°C.) | % M DAA to DMK | % M DAA to MO | % M 4H2H to 3E2H |
|---|---|---|---|---|
| 0 | 50 | 0.0 | 0.0 | 0.0 |
| 15 | " | 0.6 | 9.6 | 10.0 |
| 80 | " | 1.9 | 29.5 | 24.7 |
| 145 | " | 2.5 | 39.1 | 34.2 |
| 210 | " | 2.9 | 45.4 | 40.9 |
| 275 | " | 3.1 | 50.0 | 45.3 |
| 0 | 65 | 0.0 | 0.0 | 0.0 |
| 15 | " | 2.0 | 23.6 | 19.3 |
| 80 | " | 4.1 | 49.9 | 44.3 |
| 145 | " | 5.3 | 57.5 | 53.9 |
| 210 | " | 5.9 | 62.2 | 61.0 |
| 275 | " | 6.0 | 64.2 | 65.1 |

EXAMPLE 7

4-Hydroxy-2-heptanone/Diacetone Alcohol Dehydration Reaction

A 150 ml jacketed glass reactor was equipped with a thermocouple, magnetic stirrer, feed and sample ports, and an overhead condenser. The reactor was maintained under positive $N_2$ atmosphere by connecting the condenser vent line to a $N_2$ bubbler. Fifty ml (46.5 grams) of mesityl oxide heavy ends from the current MIBK process (the reaction medium for the dehydration reaction step), which contained the $H_2SO_4$ catalyst, was added to the reactor.

The reactor was heated by circulating through the jacket silicone oil from a temperature controlled bath. As the temperature rose light ends present in the MO heavy ends distilled out and collected in the receiving flask attached to the condenser. This fraction was removed just before the beginning of the feed addition.

The feed mixture, which contained DAA and 4H2H in 70:30 weight ratio, was pumped through an ⅛" stainless steel tube feed-preheater and added to the reactor at a rate of 4.0 ml/minute. As soon as the feed addition was started the product began to collect. Five fractions of the product and five samples of the reaction bottoms were collected during the course of the experiment which was conducted over a period of 70 minutes. The product fractions were separated into aqueous and organic phases. The reaction bottoms was also collected. The various fractions were analyzed by GC using an internal standard. GC composition and weight data were used to perform material balance.

This process was conducted twice, once in the 129°–133° C. temperature range with the second in the 142°–145° C. range. The results showed 98–99% recovery of materials, 91–92% conversion of DAA, 96–97% conversion of 4H2H, 95–97% DAA to MO/DMK selectivity, and 95–100% 4H2H to 3E2H/4E2H isomers selectivity.

This example illustrates that DAA and 4H2H produced during coproduction are converted to products simultaneously with high selectivities and very similar rates.

EXAMPLE 8

Hydrogenation of 3- and 4-Hepten-2-one/Mesityl Oxide Mixture over Pd-C Catalyst

A 500 ml Zipperclave was equipped with pressure regulated $H_2$ and $N_2$ lines with check valves, pressure relief valve, a Doric controller for temperature control, and a sampling line with external cooling coil. The feed for the hydrogenation experiment was prepared by adding 15.90 grams of mesityl oxide, 15.07 grams of 3- and 4-hepten-2-one to 290.1 grams of iso-octane. n-Decane internal standard, 1.0482 grams, was added to the feed.

The feed (after removing—2 ml for GC analysis) and 5.02 grams of Pd-on-carbon catalyst (0.5% Pd catalyst) commercially available as "CALSICAT S-89 205, E-156" from the Calsicat Company, were added to the Zipperclave vessel and stirred. Air in the vessel was replaced with hydrogen by pressurizing and de-pressurizing three times each with 30 PSIG $N_2$ and 100 PSIG $H_2$. The reaction was started by pressurizing the vessel with $H_2$ from the 100 PSIG constant pressure $H_2$ line and turning on the temperature controller. The reaction temperature increased to the set point of 100° C. over a period of 17 minutes and then remained in the 98°–100° C. range. The reaction pressure remained in the 100–125 PSIG range. The samples were centrifuged to settle the catalyst and analyzed by GC using DX-4 column.

Table 5 shows the conversion of intermediates and the selectivities of the products.

This example shows that conversion of alehydrated cross aldol reaction products is nearly 100%. Selectivities of nearly 100% of reactions to final products (MIBK and MNAK) are also attained. This avoids prior art problems of creating a complex mixture of numerous ketones and aldehydes such as is common in one-step methods.

TABLE 5

| Hydrogenation of 3- and 4-Hepten-2-one/Mesityl Oxide Mixture over Pd-C Catalyst | | | | | | | |
|---|---|---|---|---|---|---|---|
| Rxn Time | Temp | % M Conversions | | % M Selectivities | | | |
| (Min) | (°C.) | MO | 3 + 4E2H | MIBK | MIBC | MNAK | MNAC |
| 0 | 22 | 0.0 | 0.0 | | | | |
| 17 | 100 | 0.7 | 76.6 | 100.0 | 0.0 | 100.0 | 0.0 |
| 32 | " | 40.1 | 98.4 | 100.0 | 0.0 | 100.0 | 0.0 |
| 47 | " | 74.2 | 99.7 | 100.0 | 0.0 | 100.0 | 0.0 |
| 62 | " | 93.2 | 100.0 | 99.9 | 0.1 | 100.0 | 0.0 |
| 77 | " | 99.2 | 100.0 | 99.9 | 0.1 | 100.0 | 0.0 |
| 92 | " | 100.0 | 100.0 | 99.9 | 0.1 | 99.9 | 0.1 |
| 122 | " | 100.0 | 100.0 | 99.8 | 0.2 | 99.8 | 0.2 |

EXAMPLE 9

Hydrogenation of 3- and 4-Hepten-2-one/Mesityl Oxide Mixture over Pd-C Catalyst

The procedure of Example 8 was repeated using 319.0 grams of feed made from 15.04 grams of mesityl oxide, 15.05 grams of 3- and 4-hepten-2-one, 290.08 grams of iso-octane, and 1.026 grams of n-decane internal standard and 0.253 gram of a 5% Pd-on-carbon catalyst from Alfa Chemical Company. Table 6 shows the conversion of intermediates and the selectivities of the products.

This example shows that conversion of dehydrated cross aldol reaction products is nearly 100%. Selectivities of nearly 100% of reactions to final products (MIBK and MNAK) are also attained. This avoids prior art problems of creating a complex mixture of numerous ketones and aldehydes such as is common in one-step methods.

TABLE 6

| Hydrogenation of 3- and 4-Hepten-2-one/Mesityl Oxide Mixture over Pd-C Catalyst | | | | | | | |
|---|---|---|---|---|---|---|---|
| Rxn Time | Temp | % M Conversions | | % M Selectivities | | | |
| (Min) | (°C.) | MO | 3 + 4E2H | MIBK | MIBC | MNAK | MNAC |
| 0 | 24 | 0.0 | 0.0 | | | | |
| 17 | 100 | 64.9 | 100.0 | 99.8 | 0.2 | 99.9 | 0.1 |
| 32 | " | 100.0 | 100.0 | 99.7 | 0.3 | 9.99 | 0.1 |
| 47 | " | 100.0 | 100.0 | 99.6 | 0.4 | 99.9 | 0.1 |
| 62 | " | 100.0 | 100.0 | 99.6 | 0.4 | 99.9 | 0.1 |
| 77 | " | 100.0 | 100.0 | 99.6 | 0.4 | 99.9 | 0.1 |

TABLE 6-continued

Hydrogenation of 3- and 4-Hepten-2-one/Mesityl Oxide Mixture over Pd-C Catalyst

| Rxn Time (Min) | Temp (°C.) | % M Conversions | | % M Selectivities | | | |
|---|---|---|---|---|---|---|---|
| | | MO | 3 + 4E2H | MIBK | MIBC | MNAK | MNAC |
| 92  | "  | 100.0 | 100.0 | 99.6 | 0.4 | 99.8 | 0.2 |
| 107 | "  | 100.0 | 100.0 | 99.6 | 0.4 | 99.8 | 0.2 |
| 122 | "  | 100.0 | 100.0 | 99.6 | 0.4 | 99.8 | 0.2 |
| 137 | ". | 100.0 | 100.0 | 99.6 | 0.4 | 99.8 | 0.2 |

EXAMPLE 10

Hydrogenation of Mesityl Oxide/3-Hepten-2-one Mixture over Fixed Bed Pd-on-Alumina Catalyst A Pd catalyst (0.5% Pd on alumina, Calsicat E144 SDU, 1/16") was used in this example. Five to ten grams of the catalyst, diluted with SiC (8–10 mesh particles), was packed in a 15.5" long catalyst section of a 0.67" ID stainless steel tubular reactor. The catalyst section of the reactor was equipped with a 0.25" OD stainless steel tube which contained the thermocouples for measuring the catalyst bed temperatures and the catalyst was held in the annular space between the reactor wall and the thermocouple tube. The preheater section above the catalyst bed was packed with SiC. The reactor was heated by an electrical furnace. The catalyst was activated under flowing hydrogen at a pressure of 20 PSIG by gradually raising the temperature from room temperature to a maximum of 100° C. The activation was completed by holding at the maximum temperature for two hours.

Hydrogenation of MO/3E2H was carried out as follows. A liquid feed comprising 90% w heptane, 8% w mesityl oxide, and 2% w 3-hepten-2-one was mixed with hydrogen, vaporized in a heat exchanger, and the vapor was fed to the reactor. The feed rates, reactor pressure, and the average catalyst bed temperature were controlled. The reactor effluent was cooled to 10° C. and the liquid and gaseous products were separated. Several runs were conducted by varying the reactor pressure from 20 to 60 PSIG, liquid feed rate from 13 to 52 WHSV, molar ratio between hydrogen and the unsaturated ketones in the liquid feed from 1.2 to 2.2, and the average catalyst bed temperatures from 165° to 207° C.

Samples of the liquid product were analyzed by a GC method (DX-4 column) to determine the % weight composition of the product. MO conversion of 81 to 99.8% and 3E2H conversion of 94 to 99.9% were obtained. MO to MIBK selectivity of 99% and 3E2H to MNAK selectivity of 99% were obtained. This example illustrates that MO and 3E2H produced during coproduction are readily converted to products simultaneously with high selectivities.

EXAMPLE 11

Hydrogenation of Mesityl Oxide/3-Hepten-2-one Mixture over Fixed Bed Ni Catalyst A Ni hydrogenation catalyst (Ni on alumina/CaO, purchased from United Catalysts Inc as G-65 Catalyst) was reduced in size to 10–12 mesh particles. Five to ten grams of the catalyst, diluted with SiC (8–10 mesh particles), was packed in a 15.5" long catalyst section of a 0.67" ID stainless steel tubular reactor. The catalyst section of the reactor was equipped with a 0.25" OD stainless steel tube which contained the thermocouples for measuring the catalyst bed temperatures and the catalyst was held in the annular space between the reactor wall and the thermocouple tube. The preheater section above the catalyst bed was packed with SiC. The reactor was heated by an electrical furnace. The catalyst was activated under flowing hydrogen at a pressure of 20 PSIG by gradually raising the temperature from room temperature to a maximum of 325° C. The activation was completed by holding at the maximum temperature for two hours.

Hydrogenation of MO and 3E2H occurred as follows. A liquid feed comprised of 90% w heptane, 8% w mesityl oxide, and 2% w 3-hepten-2-one was mixed with hydrogen, vaporized in a heat exchanger, and the vapor was fed to the reactor. The feed rates, reactor pressure, and the average catalyst bed temperature were controlled. The reactor effluent was cooled to 10° C. and the liquid and gaseous products were separated.

Samples of the liquid product were analyzed by a GC method (DX-4 column) to determine the % weight composition of the product. Several runs were conducted by varying the reactor pressure from 40 to 75 PSIG, liquid feed rate from 7 to 54 WHSV, molar ratio between hydrogen and the unsaturated ketones in the liquid feed from 1.2 to 2.4, and the average catalyst bed temperatures from 173° to 204° C. Mesityl oxide conversion of 60 to 99.9% and 3-hepten-2-one conversion of 93.6 to 99.8% were obtained. Mesityl oxide to methyl isobutyl ketone selectivity of 90 to 99% and 3-hepten-2-one to methyl n-amyl ketone selectivity of 75 to 99% were obtained.

This example illustrates the use of a Ni based catalyst in this step of the reaction.

EXAMPLE 12

Coproduction

A feed mixture comprising between 86.2 and 96.4 w % DMK, from 1.9 to 3.0 w % NBAD, and from 1.4 to 16.8 w % water was passed in down flow mode over "A-26" catalyst at a WHSV in the range of 10 (based on the weight of wet catalyst) in the Cross Aldol Reaction step (23) of the process shown in FIG. 2.

$H_2SO_4$ was used as the catalyst in the dehydration reaction. A Ni-on alumina catalyst was used to catalyze the hydrogenation step. Temperature and pressure conditions were as noted in the description of FIG. 2 in the Detailed Description of the Invention except that steam was not introduced into the dehydration reaction/distillation column and no steps were taken to reduce residence time therein.

Samples were analyzed by Karl-Fischer water titration, acid-base titration, and GC methods. Analysis showed that MIBK and MNAK were produced simultaneously.

EXAMPLE 13

Coproduction with process modifications (Prophetic)

A feed mixture comprising from 86.2 to 96.4 w % DMK, from 1.9 to 3.0 w % NBAD, and from 1.4 to 16.8 w % water is added to the process shown and described in FIG. 2 at the Cross Aldol Reaction step and passed in down flow or upflow mode over the A-26 catalyst at a WHSV in the range of 5–25 (based on the weight of wet activated catalyst). The reaction temperature is maintained in the 10°–45° C. range. The process is modified in the dehydration step by a combination of raising the reaction temperature and injecting steam to completely recover the MO/3E2H product mixture. The reaction temperature is raised to the 145°–185° C. range and steam is added at a rate that corresponds to a steam to unsaturated ketones (MO+3E2H) weight ratio of 0 to 0.5.

At Separation Step 37 in FIG. 2, the MIBK: MNAK ratio is 0.7:0.3. This product mixture is further separated into pure MIBK and MNAK. This example shows that the claimed process can be used to obtain good yields of MNAK and MIBK in commercially significant quantities in a coproduction process. It also shows that modification of the dehydration step can preclude the loss of 3E2H into heavy ends. Overall process selectivities between 85–89% are achieved.

EXAMPLE 14

One-step DMK/NBAD Cross-Aldol Reaction over Fixed Bed A-26 Catalyst (Comparative)

A reactor consisting of a feed pre-heater (jacketed stainless steel tube, 1/8" ID×15"), a reactor tube (jacketed stainless steel tube, 0.5" ID×12") equipped with a thermocouple, a product cooler (jacketed stainless steel tube, 1/8" ID×15"), and a back-pressure regulator was set up to conduct a one-step cross-aldol reaction.

A-26 ion-exchange resin catalyst (purchased from Aldrich Chemical Co.), 32.1 grams in moist form, was added to the reactor and the void space above the catalyst was filled with a loose plug of glass wool. The catalyst was activated at room temperature and atmospheric pressure by pumping 1.0N NaOH solution through the bed, in upflow mode, at a rate of 1.6 ml/min for a period of 3.0 hours. The catalyst was then washed by pumping $CO_2$-free deionized water at a rate of 4 ml/min until the eluent was neutral (pH=7–8) to pH test paper.

A DMK/NBAD mixed feed (containing approximately 9:1 v/v) was prepared. Titration of the feed showed the presence of 80 ppmw acids (calculated as acetic acid), Karl-Fischer water analysis showed the presence of 0.6% w water, and GC analysis showed the presence of 11.4% w NBAD and 88.0% w DMK. The feed, maintained under Ar atmosphere, was pumped upflow through the catalyst bed at a rate of 1.3 ml/min (WHSV of 2 based on the weight of the moist resin) for a period of ten hours. The reactor pressure was maintained at 800 PSIG. During the first five hours, the reaction temperature was maintained around 68° C. by circulating to the feed preheater and the reactor jackets hot water at 60° C. During the second five hours, the reaction temperature was maintained around 83° C. by circulating hot water at 75° C. Product fractions were collected every hour.

Feed and product samples were analyzed by a GC method which employed a 60 meter DX-4 column and MIBK as internal standard. The samples were also analyzed by a Karl-Fischer water analysis method (Hydranal working medium K as solvent and composite 5K as titrant) suitable for the analysis of ketones. The conversion and selectivity results are given in Table 7.

TABLE 7

One-Step DMK/NBAD Cross-Aldol Reaction over Fixed Bed A-26 Catalyst (Comparative)

| Run Time (Hour) | Rxn Temp (°C.) | WHSV* (G/G/Hr) | % M Conversions DMK | % M Conversions NBAD | Sel, % M DMK to C6 | Sel, % M DMK to C7 | Sel, % M NBAD to C7 | Prod H2O (% W) | Calculated Feed H2O (% W) |
|---|---|---|---|---|---|---|---|---|---|
| 1 | 66 | 2.0 | 15.6 | 99.4 | 36.6 | 43.5 | 65.1 | 25.8 | 24.1 |
| 2 | 68 | 1.9 | 14.2 | 99.6 | 30.7 | 39.6 | 53.8 | 14.6 | 11.9 |
| 3 | 68 | 1.8 | 15.0 | 99.7 | 34.3 | 20.8 | 29.8 | 9.4 | 5.8 |
| 4 | 69 | 1.9 | 16.1 | 99.8 | 38.0 | 9.2 | 14.2 | 7.2 | 3.0 |
| 5 | 69 | 1.8 | 17.6 | 99.9 | 39.2 | 4.9 | 8.3 | 6.2 | 1.5 |
| 6 | 84 | 1.8 | 20.6 | 99.9 | 42.2 | 2.0 | 3.9 | 6.3 | 0.9 |
| 7 | 84 | 1.8 | 22.9 | 99.9 | 36.8 | 1.2 | 2.6 | 6.4 | 0.4 |
| 8 | 83 | 1.7 | 21.4 | 99.9 | 38.8 | 1.2 | 2.4 | 6.3 | 0.6 |
| 9 | 83 | 1.8 | 21.7 | 99.9 | 37.8 | 1.2 | 2.4 | 6.2 | 0.5 |
| 10 | 82 | 1.8 | 21.3 | 99.9 | 37.8 | 1.3 | 2.7 | 6.1 | 0.5 |

*Based on moist resin added to reactor

This example shows that commercial coproduction of both MIBK and MNAK is impractical in one-step processes employing ordinary catalyst systems.

What is claimed is:

1. A process for coproducing methyl n-amyl ketone and methyl isobutyl ketone by aldol condensation comprising:

reacting an acid free feed of dimethyl ketone and n-butyraldehyde in the presence of a fixed bed basic ion exchange cross aldol catalyst with a stream of at least about 1% wt water (basis total weight of feed) pumped through said catalyst to produce a first intermediate mixture;

dehydrating said first intermediate mixture in the presence of steam at a steam to total unsaturated ketone ratio (by weight) of up to about 0.5 and a catalytic quantity of a member of the group consisting of $H_2SO_4$, $NaHSO_4$, and sulfonic acid resins to produce a second intermediate mixture; and hydrogenating said second intermediate mixture in the presence of a stream of hydrogen and a hydrogenation catalyst to produce a product mixture comprising methyl iso-butyl ketone and methyl n-amyl ketone wherein said cross aldol catalyst remains viable for at least 25 days.

2. The process of claim 1 wherein said reaction of acetone and n-butyraldehyde occurs between about 1 and 10 atmospheres of pressure, at temperatures between about 0° and 60° C.

3. The process of claim 1 wherein said dehydration step is conducted at temperatures between about 137° C. and 174° C. and a pressure of between about 1 and 2 atmospheres.

4. The process of claim 1 wherein said hydrogenation step is conducted by contacting said second intermediate mixture with $H_2$ and said hydrogenation catalyst is selected from the group consisting of Ni, Co, Cu, Cr, Pt, Pd, Rh, Ru, Re, Ir and mixtures thereof.

5. The process of claim 4 wherein said hydrogenation step is carried out at temperatures between about 50° and 225° C. and a pressure of between about 15 and 250 PSIG.

* * * * *